(12) United States Patent  (10) Patent No.:   US 8,182,749 B2
Thomas  (45) Date of Patent:   May 22, 2012

(54) PRODUCTS AND METHODS FOR DISPENSING OF AIR FRESHENERS, DEODORIZERS OR SANITIZERS

(76) Inventor: John F. Thomas, Silver Spring, MD (US)

( * ) Notice: Subject to any disclaimer, the term of this patent is extended or adjusted under 35 U.S.C. 154(b) by 357 days.

(21) Appl. No.: 12/341,896

(22) Filed: Dec. 22, 2008

(65) Prior Publication Data

US 2009/0162244 A1    Jun. 25, 2009

Related U.S. Application Data

(60) Provisional application No. 61/016,269, filed on Dec. 21, 2007.

(51) Int. Cl.
*A62B 7/08*   (2006.01)
*A61L 9/00*   (2006.01)
(52) U.S. Cl. .............................. 422/124; 422/5; 422/123
(58) Field of Classification Search .............. 422/5, 123, 422/124
See application file for complete search history.

(56) References Cited

U.S. PATENT DOCUMENTS

| | | | | |
|---|---|---|---|---|
| 4,303,617 | A * | 12/1981 | Bryson | 422/123 |
| 5,115,975 | A * | 5/1992 | Shilling | 239/55 |
| 5,417,929 | A * | 5/1995 | Kita | 422/123 |
| 2002/0157540 | A1 | 10/2002 | Lynn | |
| 2002/0197186 | A1 | 12/2002 | Murray | |
| 2003/0097936 | A1 | 5/2003 | Maleeny | |
| 2003/0192922 | A1 | 10/2003 | Ceppaluni | |
| 2004/0094037 | A1 | 5/2004 | Maleeny | |
| 2004/0223891 | A1 | 11/2004 | Brown | |
| 2005/0031498 | A1 | 2/2005 | Held | |
| 2006/0113687 | A1 | 6/2006 | Castellano | |
| 2007/0140924 | A1 | 6/2007 | Hill | |
| 2009/0007582 | A1* | 1/2009 | Ulanov | 62/274 |

* cited by examiner

*Primary Examiner* — Kevin Joyner
(74) *Attorney, Agent, or Firm* — Scott Houtteman; Kile Park Goekjian Reed & McManus (57) ABSTRACT

A device, such as a home air freshener, which is mounted to the main positive pressure air duct of a forced air furnace heating system and or a central air conditioning system by which an outside agent, such as an air freshener, is introduced into the air duct for the distribution to areas served by the air duct system. By means of a sub-duct properly positioned in the path of the airflow, the device can create a low pressure area in the sub-duct which will draw and distribute the air freshener and thus operate with out means of outside pressure, power, or moving parts.

7 Claims, 15 Drawing Sheets

PRODUCTS AND METHODS FOR DISPENSING OF AIR FRESHENERS, DEODORIZERS OR SANITIZERS

This invention claims priority to Provisional Application No. 61/016,269 filed Dec. 21, 2007, the contents of which are hereby incorporated herein by reference.

BACKGROUND OF THE INVENTION

This invention generally pertains to the delivery of air fresheners to rooms in homes and offices, generally by way of the heating, ventilation and air conditioning (HVAC) system. In the past air freshener delivery systems operated on one of two principles: and "injection" system or a direct air pressure driven system. In the former system, a reservoir of air freshener is typically stored under high pressure. Upon transmission of certain signals, the air freshener was dispensed into the ductwork of the HVAC system and distributed throughout the home or office. These prior art devices addressed problems of regulating the timing and duration of the delivery system taking into account the two different states encountered by the device, when the HVAC blower was "on" and "off" and the seasonal switch from heating to air conditioning. The advantage of these systems was that with the proper sensors and other electronic components, these devices could be operated remotely and even automatically. The disadvantage is that these systems are complex and require periodic maintenance and are therefore relatively expensive to manufacture and service.

In the latter case, the air freshener is placed directly in the path of the airflow which carries the scent to the room. Variations include locating the air freshener in different positions along the HVAC ductwork, for example, attachment to the air vent cover. Other variations include altering the chemical makeup of the substance itself and the container holding the substance. These systems have the advantage of having no moving parts and being relative inexpensive. The disadvantage is that the system has very limited applicability to remote or automatic operation. For example, to avoid evaporation of the air freshener when the HVAC system is turned off, the user must remember to manually close the air freshener housing. Also, to distribute the product to different areas of the home or office, the user must manually position dispensers in these different areas.

In summary, these devices control the atmosphere through the release of fragrances by way of vapor/aerosol for supplying aromatic oil, deodorant, disinfectant, fumigant, fungicide, insecticide or bactericide to a room or specific area. There are also devices for emitting a vaporized substance, such as an insecticide, into the atmosphere of a room or area. However, there are no devices for the delivery of substances to multiple areas and or rooms by way of a single device. At present the only way to serve multiple areas and or rooms is by placing multiple devices in each of the areas and or rooms.

The invention disclosed herein, combines the remote or automatic operation of the "injection" system with the economical and maintenance free features of the direct air pressure driven system. The device can deliver substances to freshen air, deodorize air, and or sanitize air and surfaces. The home air freshener will expand the area or areas of delivery of any substance dependent on delivery by air, to all areas in a structure or facility being served by a forced air system. The home air freshener can be modified from the base shape and size shown in the drawings of this application to other shapes and sizes required to accommodate any substance and its container as long as the integrity of certain features is maintained. As will be described in detail below, these features are the presence of a sub-duct and the pattern of airflow through the invention.

The home air freshener invention can deliver any substance intended for air borne delivery to all areas of a structure or facility being served by a forced air device and or system.

SUMMARY OF THE INVENTION

The home air freshener invention makes it possible to deliver a desired air borne substance such as a fragrance, aromatic oil, deodorant, disinfectant, fumigant, fungicide, insecticide or bactericide, etc. to all areas and or rooms of a structure or facility as opposed to just one area or room as is presently accomplished by room air fresheners and other similar products.

The basic model of the home air freshener invention does not have any moving parts and requires no power, other than the movement of the air from the air handling device and or system to which it is attached, its size and shape can be modified and an electrical outlet added to accommodate any container and or delivery control device of the substance being introduced to the home air freshener invention for delivery to areas of the structure and or facility being served by the air handling device and or system such as but not limited to a central heating cooling system.

The home air freshener invention can be attached to existing forced air devices and or systems such as but not limited to a central heating and or air condition system of a house or any other structure with a similar forced air system such as but not limited to a rooftop unit or central forced air system of any structure and or facility.

The home air freshener invention can also be part of (built in) and if need be, be modified for a future air handling system that will use forced air and is planed for production. The invention is the means to introduce substances into chambers of positive air pressure by means of a sub-duct and the movement of the positive air pressure with in the chamber transporting the air.

DETAILED DESCRIPTION OF THE PREFERRED EMBODIMENT

The home air freshener invention is a means to transfer, transport, move, deliver any substance intended to be delivered by air to all areas and or rooms being served in a structure or facility by a forced air device and or system.

The home air freshener invention can deliver an air freshener, deodorant, and or sanitizer, etc. to each room of a house, office building, hospital, shopping mall, or any building or facility being heated and or cooled by a forced air system.

The home air freshener invention can be adapted to be used with any product by any manufacture for the control of an atmosphere in a controlled environment. The preferred embodiments of the present invention have been described and illustrated. Modifications may be made by one of ordinary skill in the art without departing from the scope and the spirit of the invention as defined in the appended claims.

Figure 1:
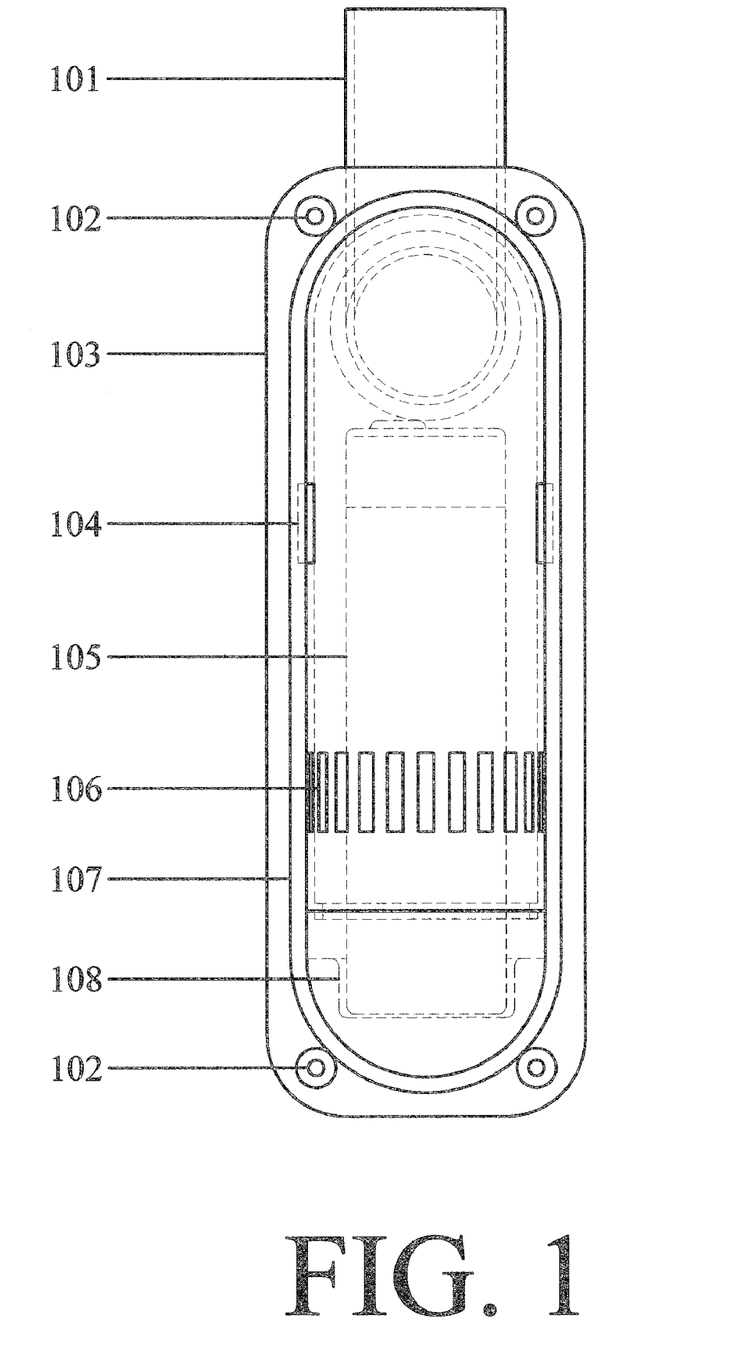
FIG. 1 illustrates is a front elevation of a preferred housing unit and sub-duct configuration.
Figure 11:
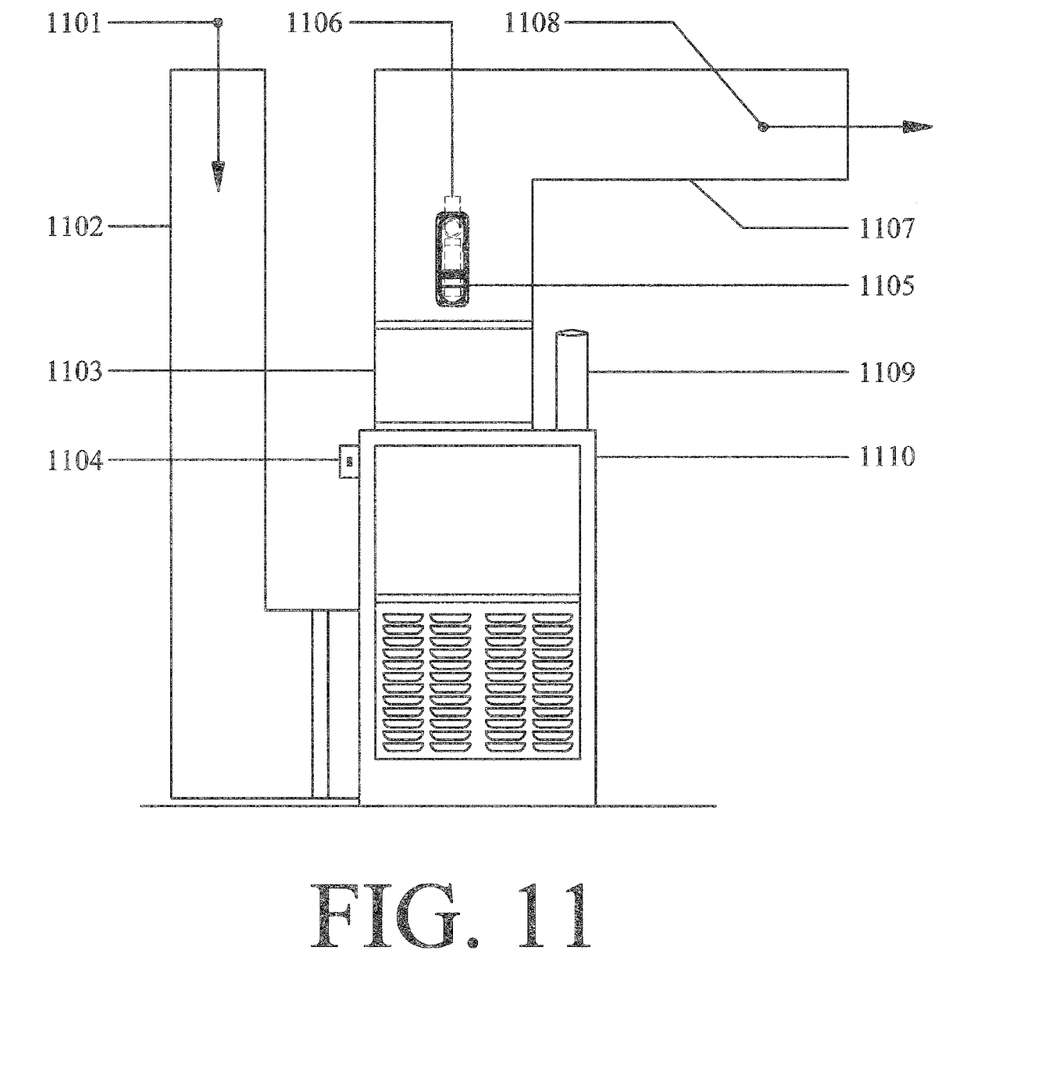
FIG. 11 illustrates a preferred embodiment of the housing unit and sub-duct in place on a typical forced air furnace found in a HVAC system.

In a preferred embodiment, shown in FIG. 1, a sub-duct 101 made of hard plastic fits inside a main supply air duct (FIG. 11, item 1107). The sub-duct preferably has a 180 degree turning radius. Screw openings 102 to receive one each self-tapping galvanized screw (preferably 4 minimum per unit) are shown anchoring the unit to main supply duct and seal gasket.

The base or housing 103 is typically made of hard plastic and consist of a back that attaches to main supply duct and bottom which holds the cradle which holds the container of air freshener. A clip anchor 104 is part of cover made of hard plastic that clips to unit base in slots of base. Air freshener is housed in a container 105. Vent holes 106 in the unit cover provides openings for out side air to enter unit on way to main air supply duct. Can be provided with damper to control air flow. The unit side cover 107 is made of hard plastic that clips on to unit base. The unit cradle 108 is recessed in the unit base and sized to hold the container of the air freshener 105.

Figure 2:
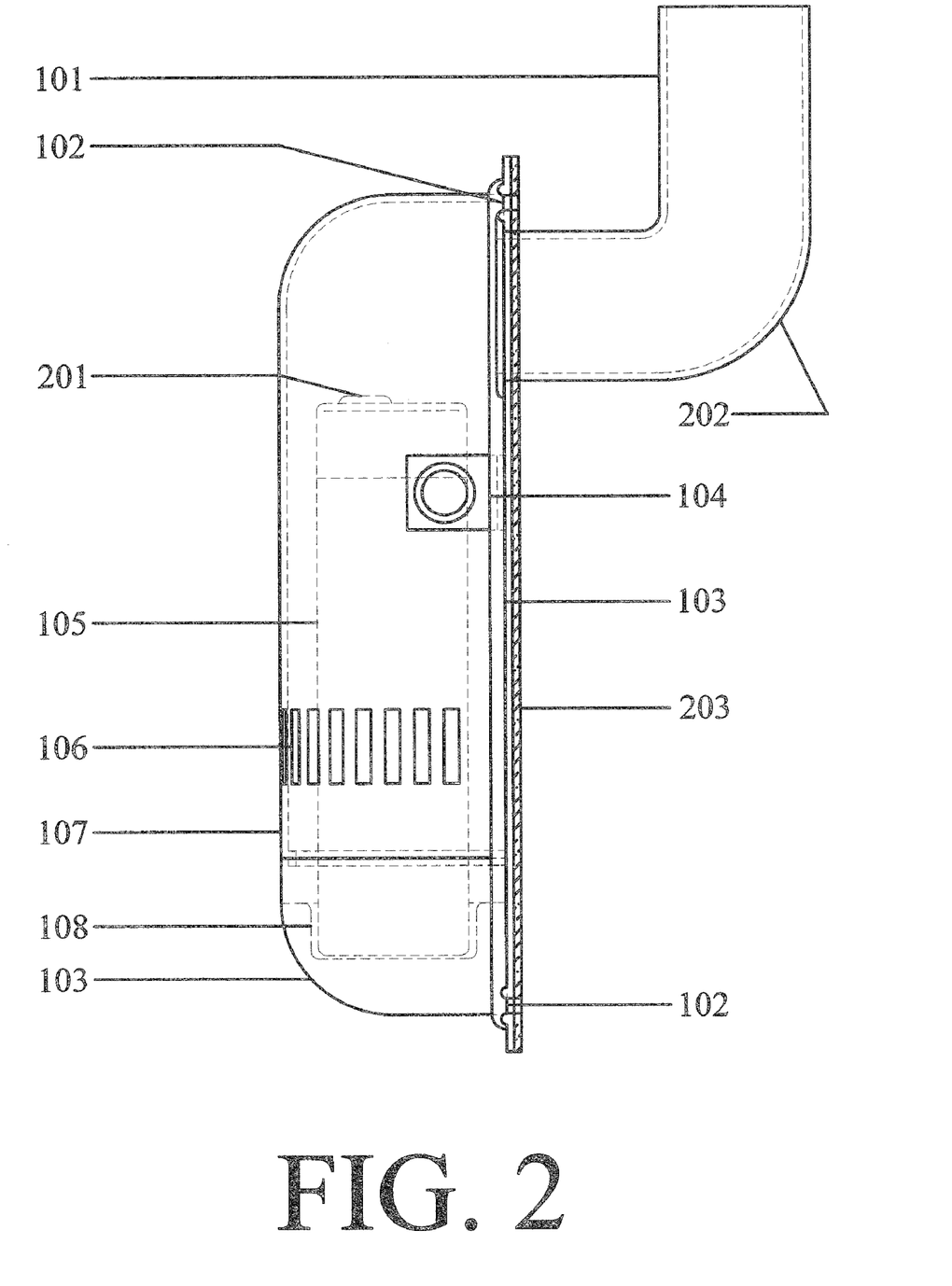
FIG. 2 is a side elevation of a preferred housing unit and sub-duct.

FIG. 2 illustrates a side elevation if the housing 103. An adjustable cover 201 on the air freshener controls the amount of sent entering air duct. The sub-duct is shown with a ninety degree elbow 202 with orients the opening of the sub-duct 101 in the direction of air flow in main air duct which creates a vacuum. An adhesive gasket 203 is attached to back of base unit and adheres to main air duct. to provide a seal between unit base and main duct. Also shown is a side view of the screw openings 102, the clip anchor 104, the vent holes 106, side cover 107 and cradle 108.

Figure 3:
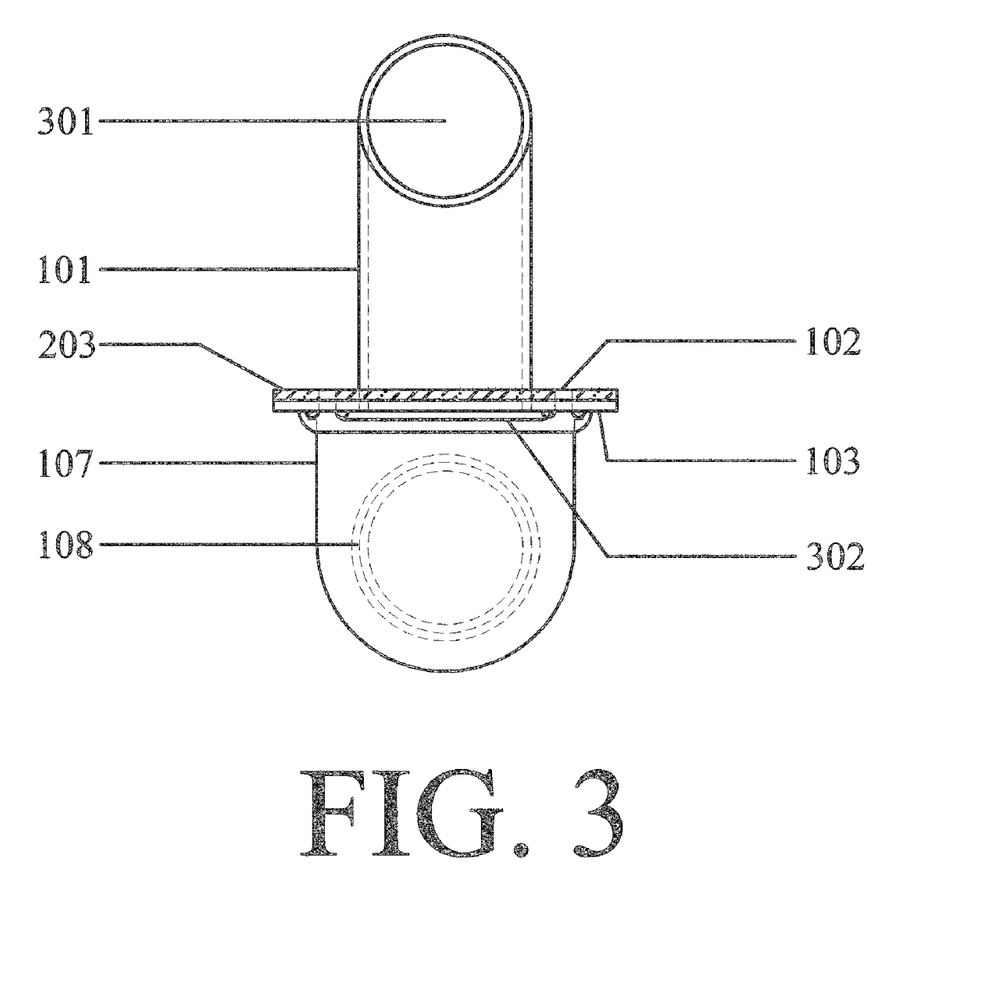
FIG. 3 is a top view of a preferred housing unit and sub-duct.

FIG. 3 illustrates the portion of the sub-duct opening 301 where outside air enters to main air duct supply carrying the scent of the air freshener. Also shown is the sub-duct 180 degrees flexible joint 302 which is used to point the sub-duct in the direction of the air flow in the main supply duct.

Figure 4A:
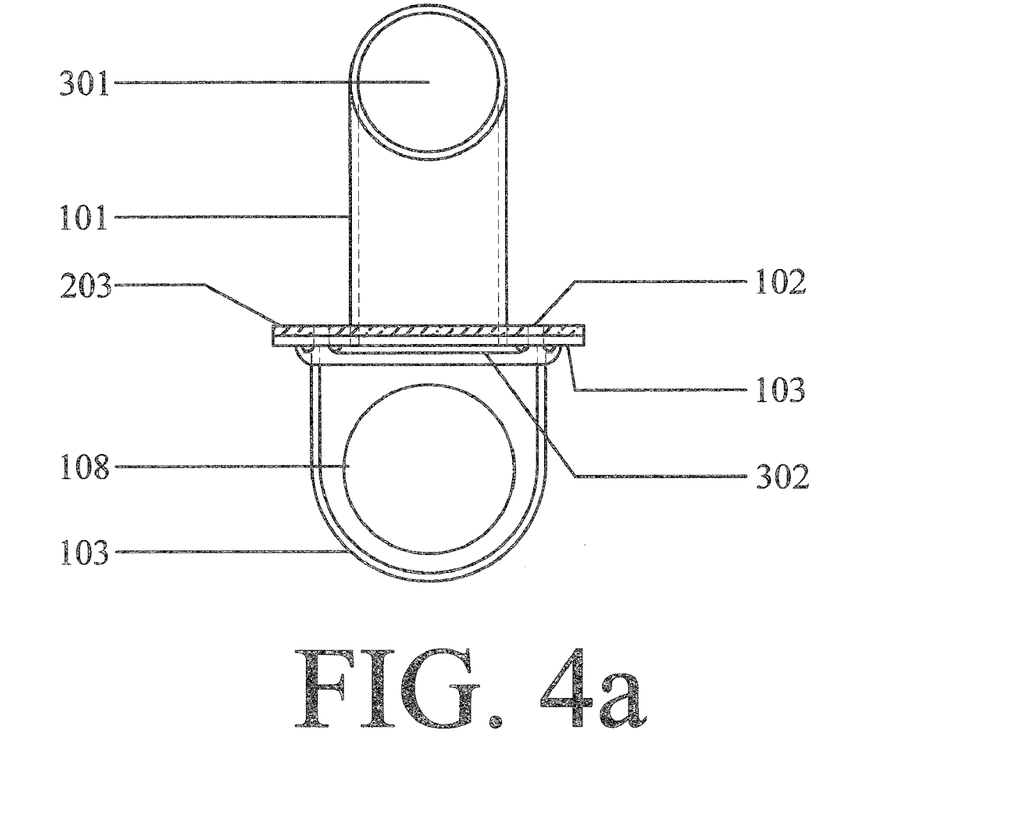
FIGS. 4a-b are a top view of the housing unit and sub-duct without a cover and with a cover, respectively.
Figure 4B:
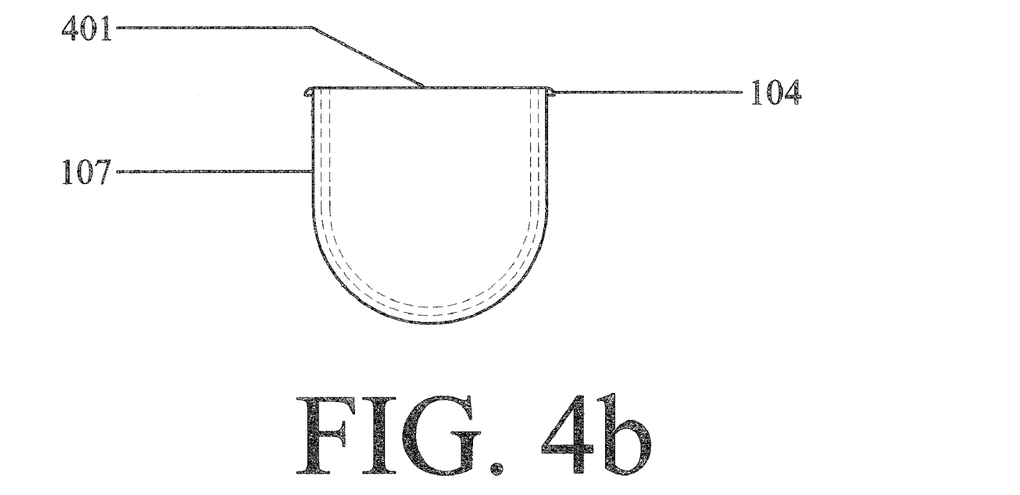

FIG. 4a shows a top view of the sub-duct opening 301, sub-duct 101, adhesive gasket 203, screw openings 102, housing 103, 180 degree joint 302, cradle 108. FIG. 4b illustrates a unit top cover 401 attached to the unit base along with the clip anchor 104 and side cover 107.

Figures 5A, 5B:
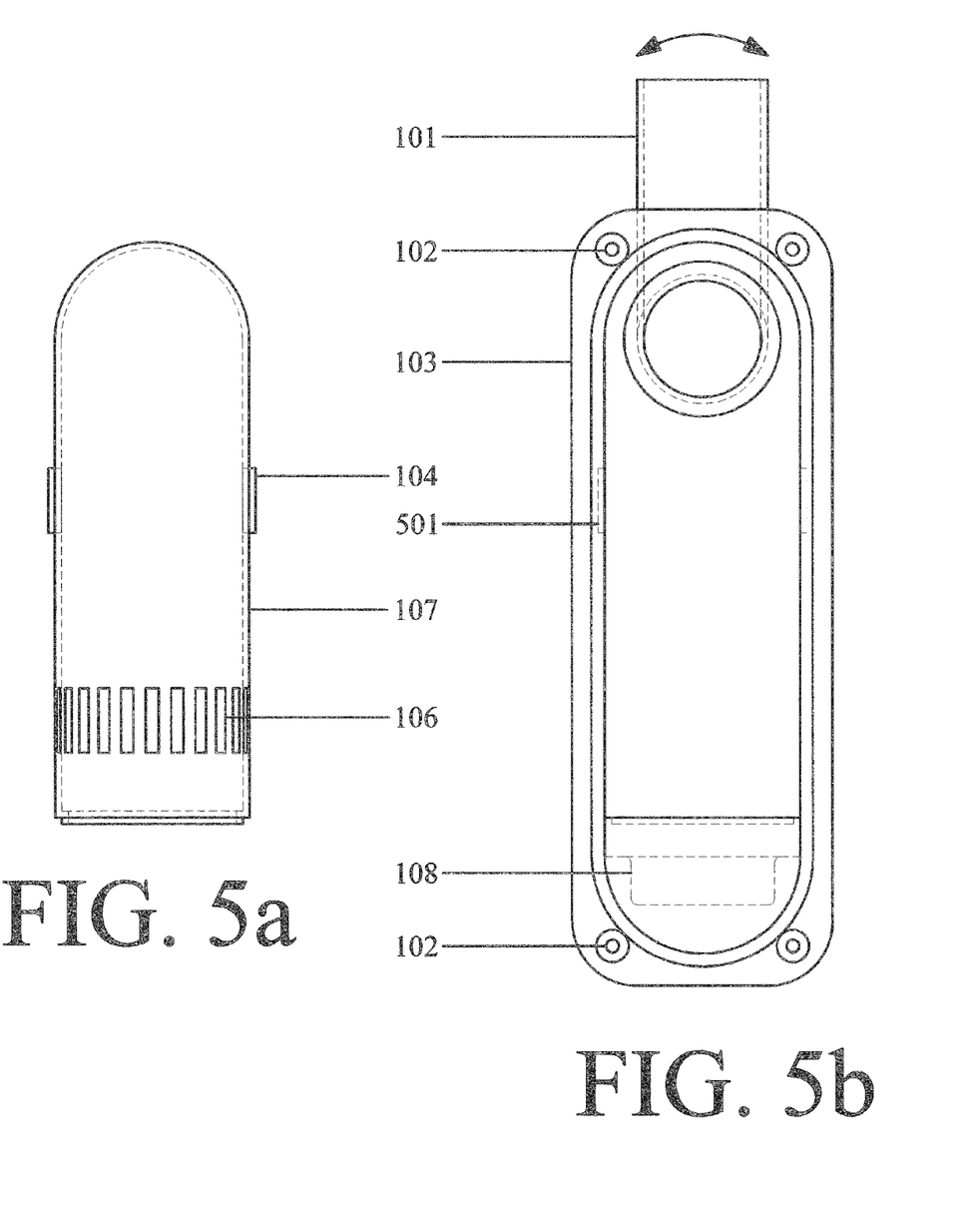
FIGS. 5a-b are front elevations of the housing unit and sub-duct without a cover and with a cover, respectively.

FIGS. 5a-b detail a preferred unit base 103 with unit base receiving slots 501 for clip anchors 104 for the base side cover 107. Also shown are the sub-duct 101, the screw openings 102, and the cradle 108.

Figures 6A, 6B:
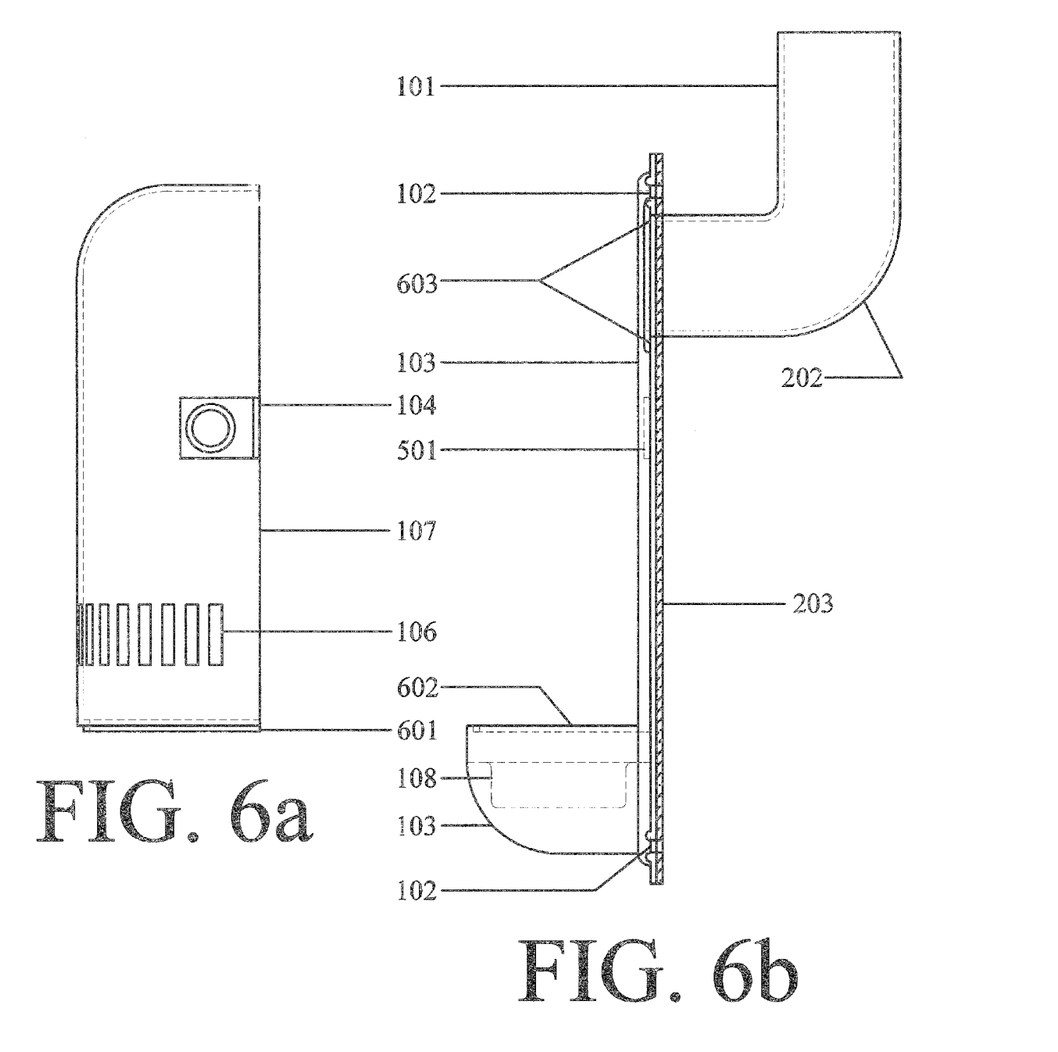
FIGS. 6a-b are side elevations of the housing unit and sub-duct without and with a cover, respectively.

In FIGS. 6a-b, the side unit cover male edge 601 is shown which fits inside female edge 602 of unit base. When a newly placed sub-duct is installed, a hole will be drilled though the main air duct and unit base in the area indicated 603. For context, other components such as the sub-duct 101 elbow 202 and screw openings 102 are also illustrated.

Figure 7A:
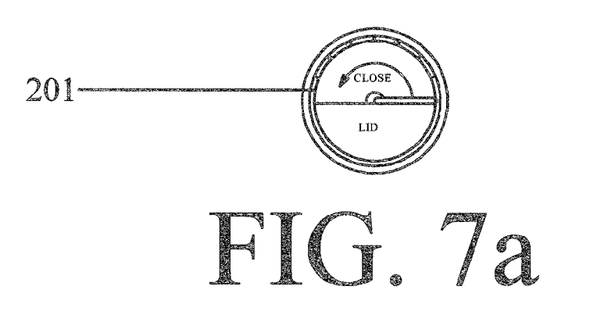
FIG. 7a-c illustrate a preferred embodiment with an adjustable opening to control the amount of air freshener entering the supply air duct system.
Figure 7B:
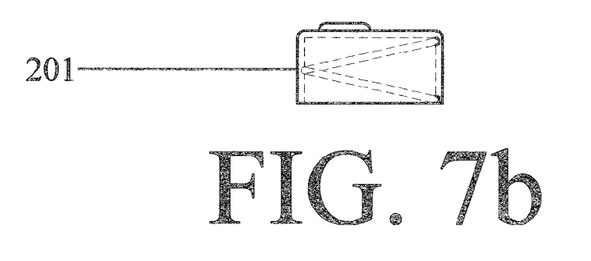
Figure 7C:
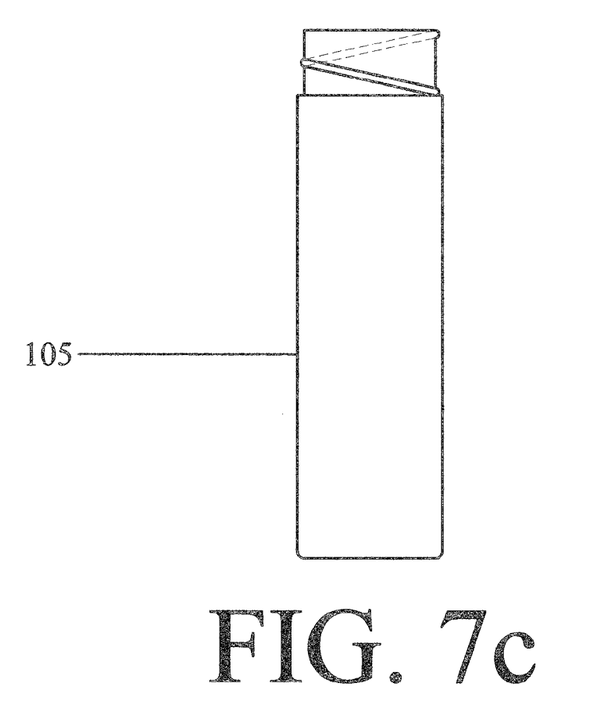
Figure 8:
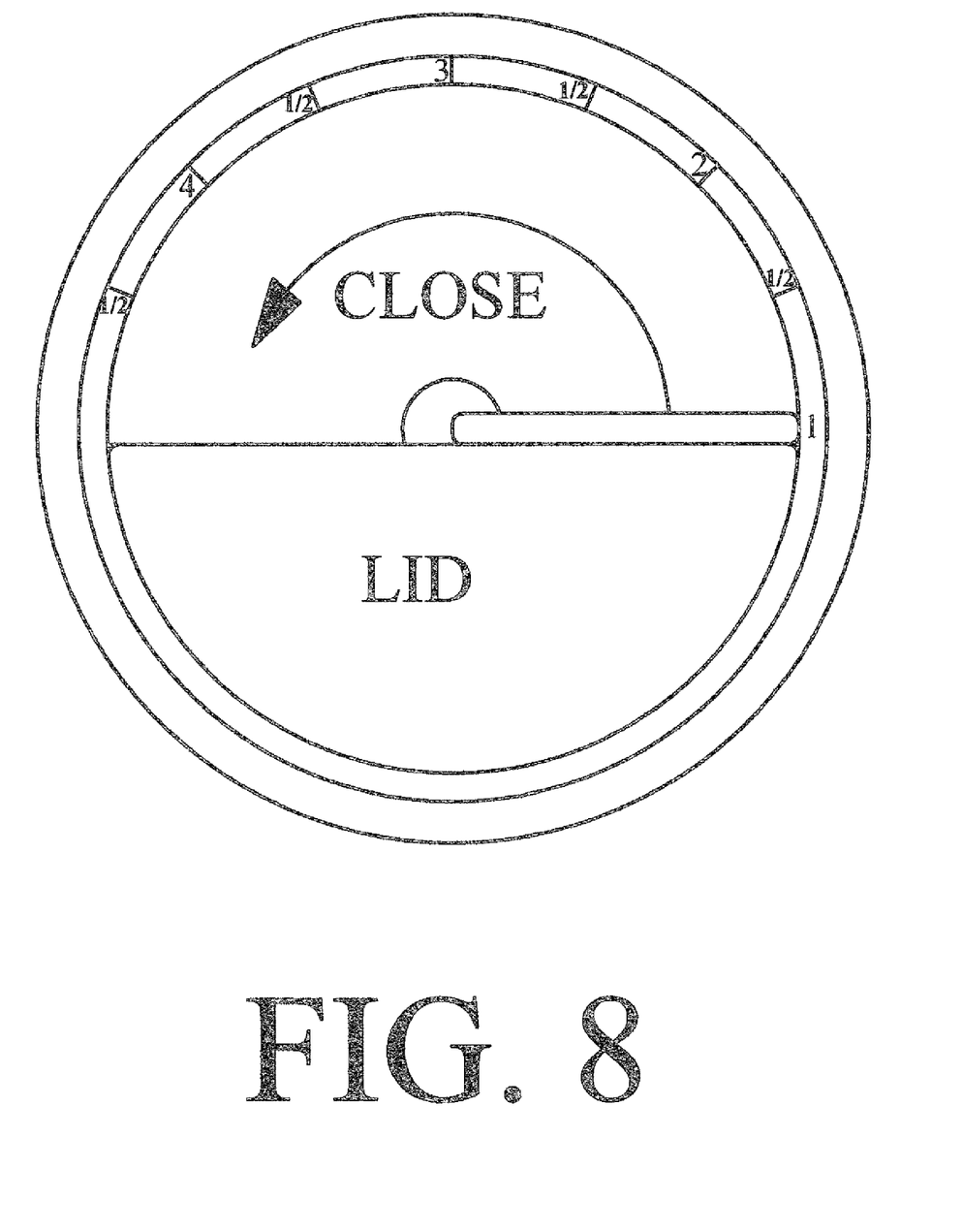
FIG. 8 is an enlarged top view of the container of air freshener lid illustrated in FIG. 7.

FIGS. 7a-c are detailed views an air freshener lid 201 covering the air freshener container 105. The lid provides for an adjustable opening to control amount of air freshener entering supply air duct system. FIG. 8 is a detailed view of the lid of FIG. 7a.

Figure 9A:
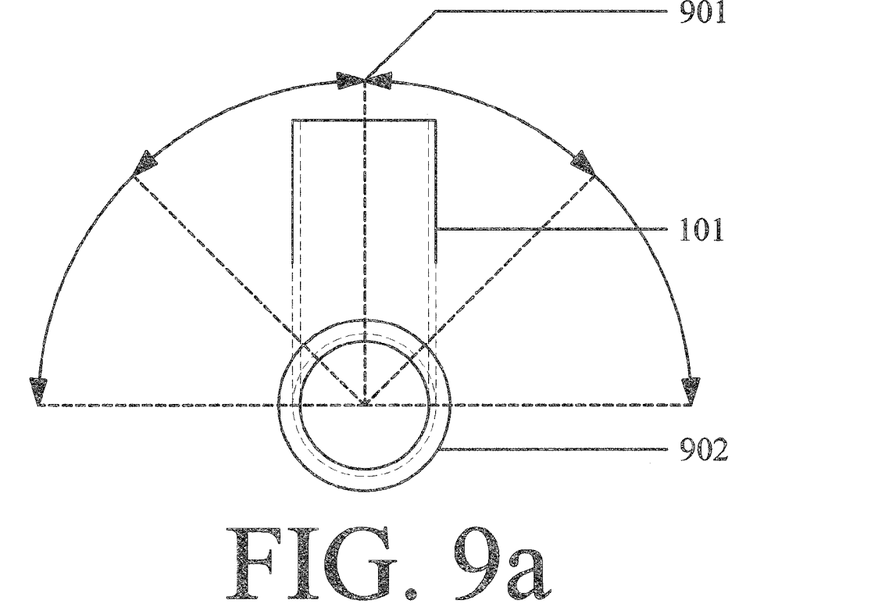
FIGS. 9a-b illustrate a front and side elevation of the sub-duct, respectively.
Figure 9B:
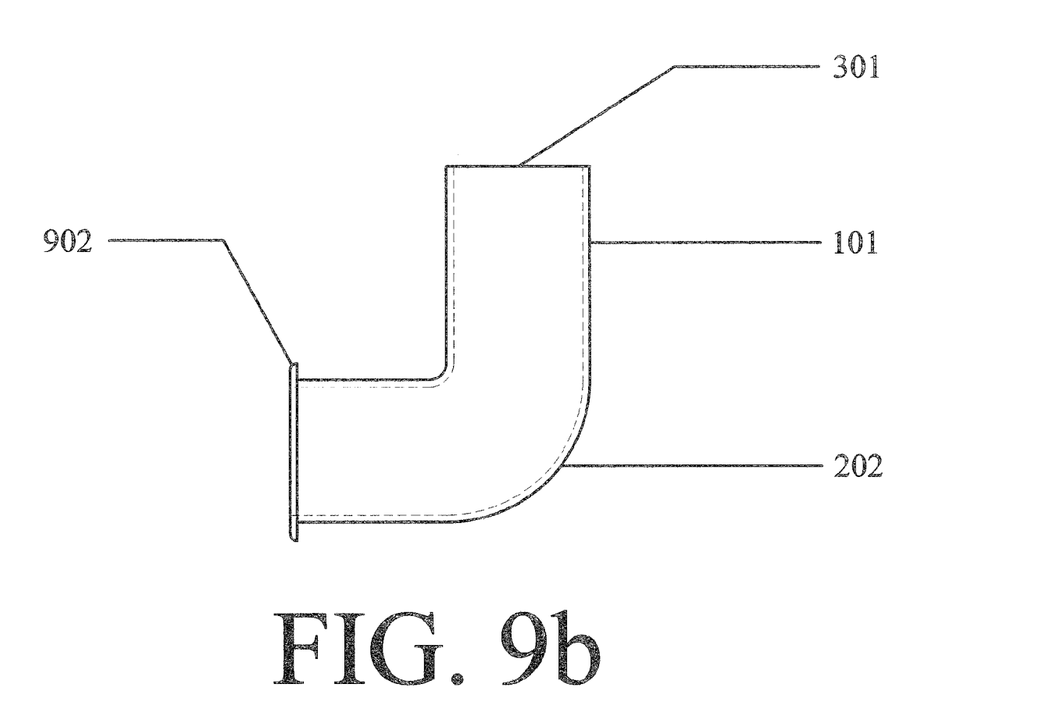

FIGS. 9a-b illustrate front and side views, respectively, of the sub-duct 101 and elbow 202 which in a preferred embodiment requires a minimum turning radius of 180 degrees 901 to point the sub-duct in direction of air flow inside of the main air supply duct. A sub-duct flange 902 is provided for placement of adhesive sealer once sub-duct has been placed in direction of air travel inside of the main positive air flow.

Figures 10A, 10B:
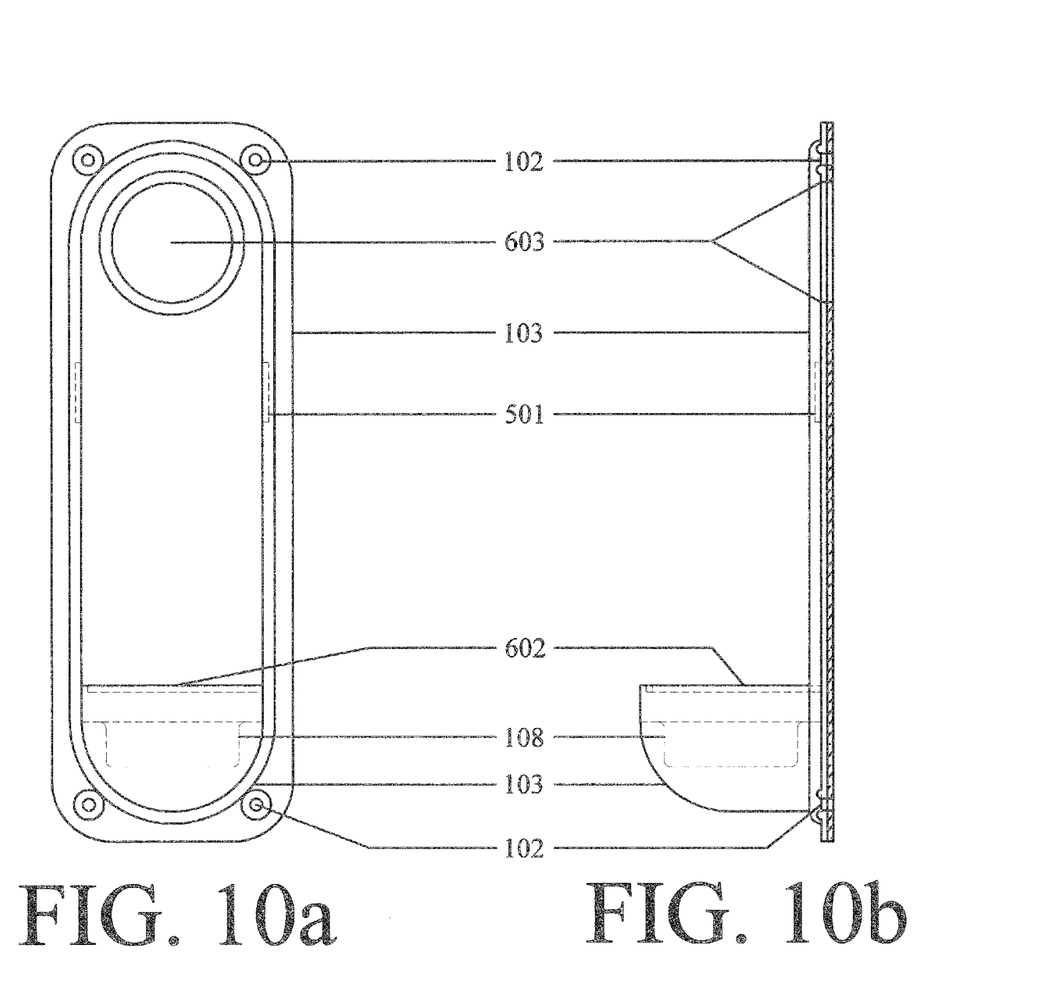
FIGS. 10a-b illustrate a front and side elevation of a sub-duct without a cover.

FIGS. 10a-c illustrate the uncovered device to further illustrate a preferred location of the hole drilled in the unit base 603 and the female edge 602 in the housing 103.

Figure 12:
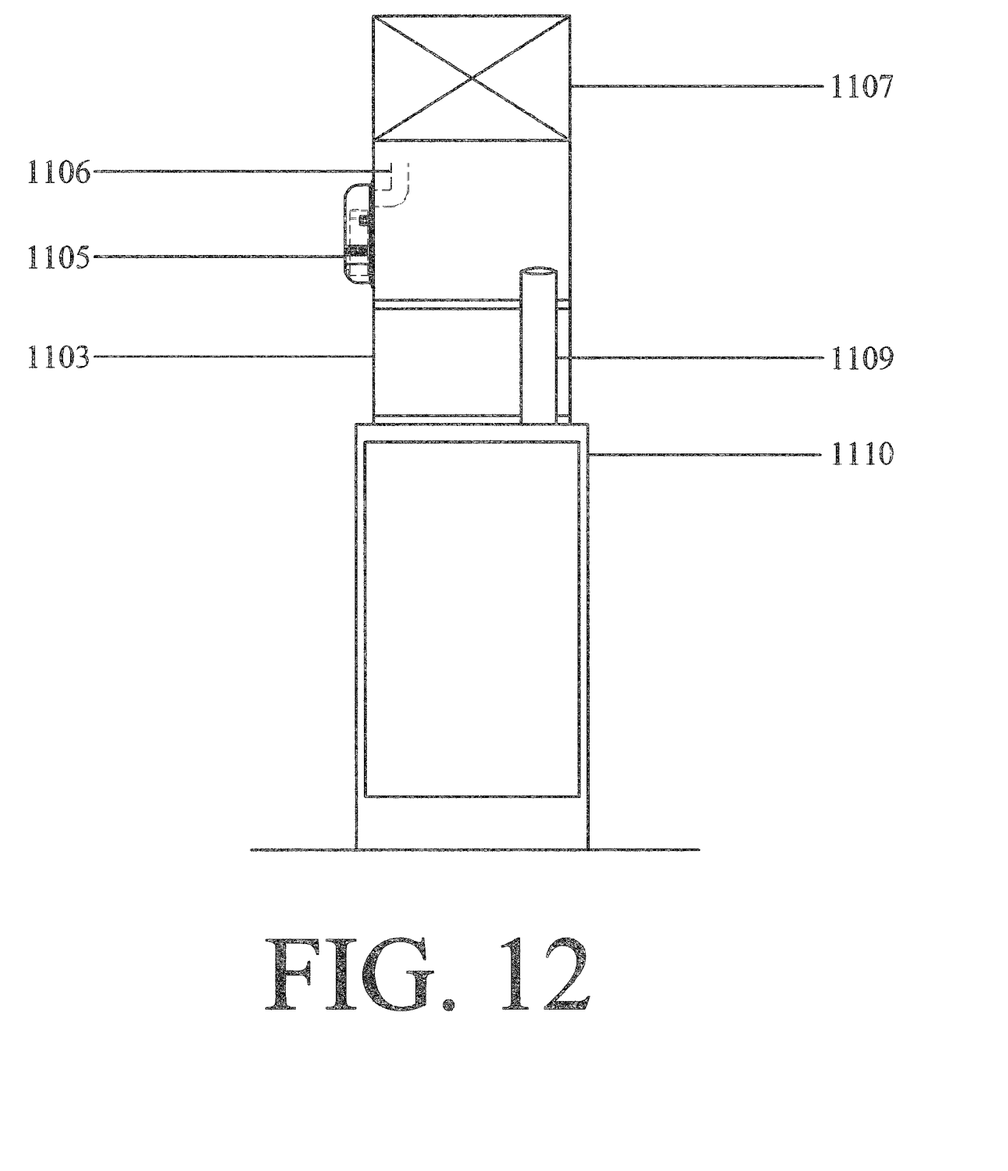
FIG. 12 is a side elevation of FIG. 11.

The device 1105 is illustrated in the context of an HVAC system in FIG. 11 which illustrates a typical forced air furnace 1110, front elevation. Shown in the figure is the direction of flow of the return air 1101 in the return air duct 1102 (negative pressure) as will as the supply air direction 1108 in main supply air duct 1107 (positive pressure). Also shown is the main return air duct 1102 and the AC coil 1103. The AC coil should not be disturbed in installing the disclosed system. The power switch 1104, the sub-duct 1106, the gas exhaust 1109 (if gas fired) are also illustrated. FIG. 12 is a side elevation of the furnace 1110 of FIG. 11 which illustrates a preferred position of the device 1105 with the sub-duct 1106 in the context of the main air supply duct 1107, the AC coil 1103 and the gas exhaust 1109.

Figure 13:
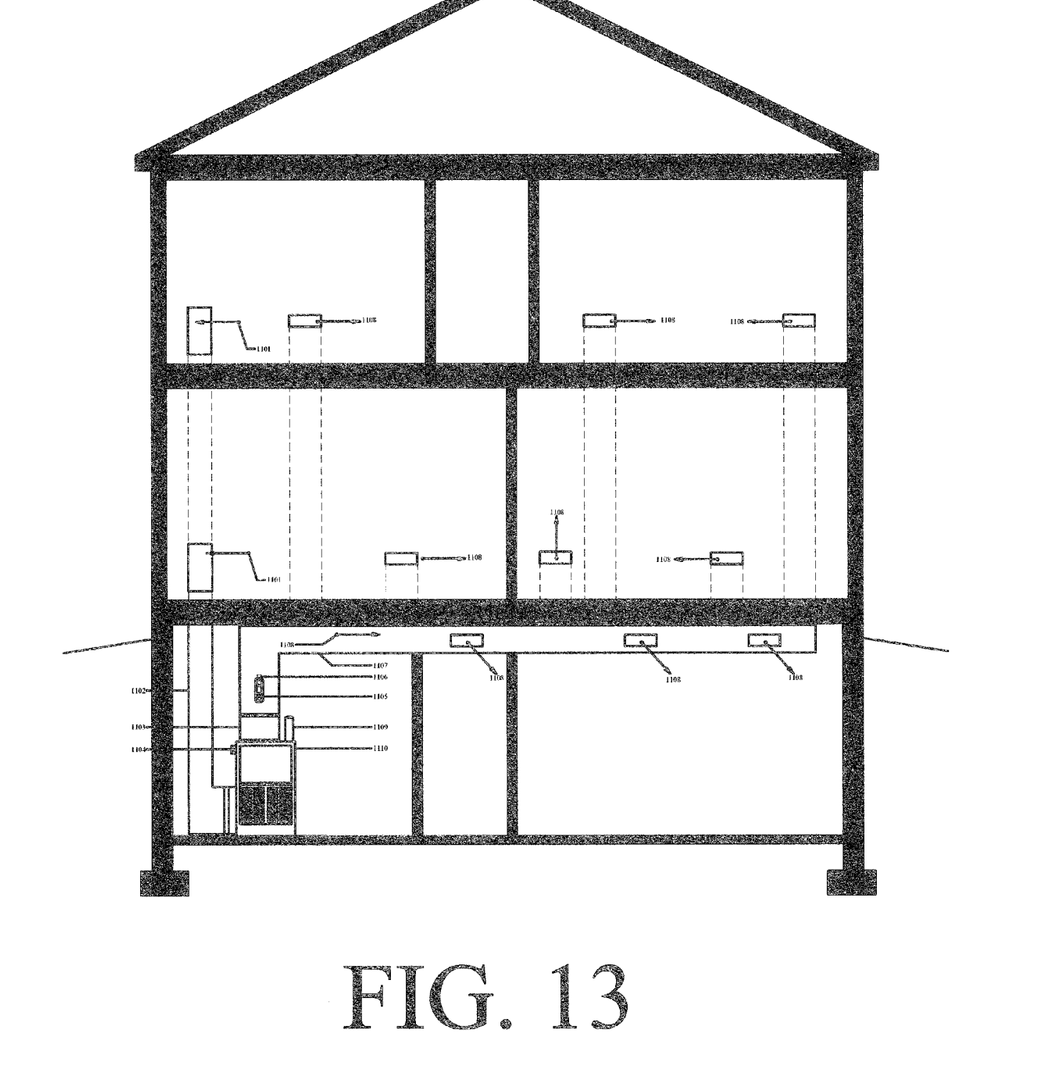
FIG. 13 illustrates a typical two story home with a preferred embodiment of the invention in place.

FIG. 13 illustrates a typical set up if the system in a two story single family home. The supply air ducts 1107 and the return air ducts 1102 are shown.

Figure 14:
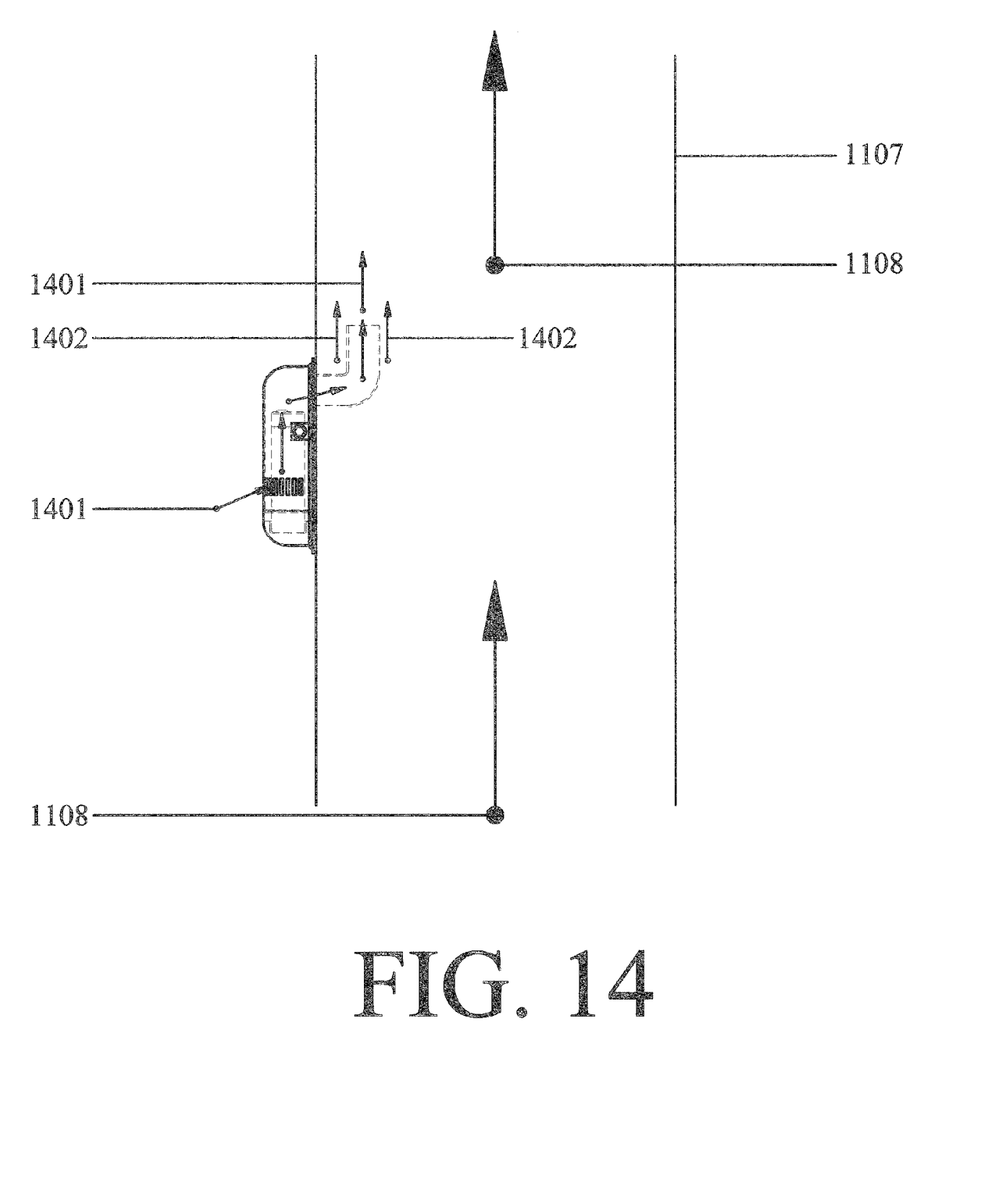
FIG. 14 is a detail side elevation illustrating a preferred positioning of the housing unit and sub-duct on the main supply air duct.
Figure 15:
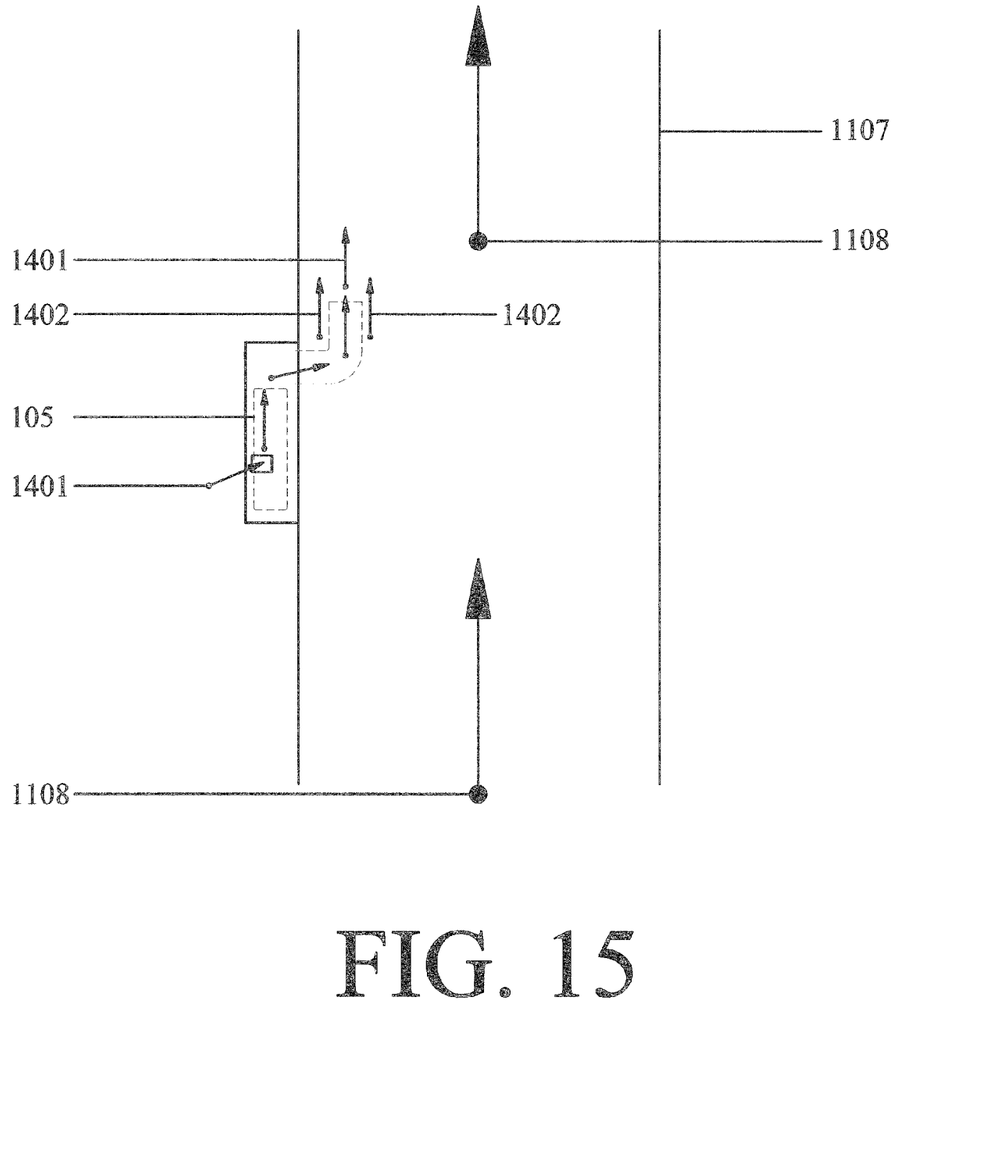
FIG. 15 is a schematic illustration of a preferred positioning of the sub-duct in the path of the airflow showing a preferred pattern of airflow around the opening of the sub-duct.

FIGS. 14 and 15 detail the air flow in the context of the device, the sub-duct and the supply air ducts 1107. In a preferred embodiment air enters the device through vents 1401 (negative pressure) and travels into the main supply air duct where indicated. This will happen, in a preferred embodiment, if the direction of airflow 1108 in the supply air duct and around the subduct 1402 is in the orientation indicated such that the opening of the sub-duct points in the same direction as the airflow.

I claim:

1. An air freshener delivery device for use with a heating, ventilation and air-conditioning system comprising:
   a housing unit mounted on a structure,
   a plurality of vent holes in said housing unit,
   a sub-duct having a first and a second opening,
   a substance to be delivered, and
   an airflow inside of said structure,
   said first opening of said sub-duct located inside of said housing unit and said second opening of said sub-duct located in the path of said airflow,
   said sub-duct openings being configured such that said airflow causes a decrease in air pressure inside of said sub-duct, 
said second opening of said sub-duct points in the same direction as the airflow such that the airflow travels past said second opening and not into said second opening, said air pressure decrease causes air, from an atmosphere outside of the structure, to be drawn through said vent holes into said housing unit and to carry said substance out of said housing unit, through said sub-duct and into said airflow, wherein said airflow delivers said substance to a destination.

2. A device as defined in claim 1 wherein said substance is selected from the group consisting of: air freshener, deodorants, disinfectants, fumigants, fungicides, insecticides and bactericides.

3. A device as defined in claim 1 further comprising:

a movable lid operable to move through multiple positions from a fully closed position to a fully open position wherein said fully closed position effectively seals said substance to be delivered in a closed container and said fully open position allows the device to operate normally.

4. A device as defined in claim 1 further comprising a movable lid which moves to a closed position when said airflow is halted to effectively seal said substance to be delivered in a closed container.

5. A device as defined in claim 1 further comprising:

a dampener operable to adjust the effective size of said vent holes and thus increase or decrease the amount of pressure drop in the sub-duct caused by said airflow.

6. A device as defined in claim 1 wherein said device further consists of no additional component having an air pressure above atmospheric air pressure.

7. A method of air freshener delivery for use with a heating, ventilation and air-conditioning system comprising:

a housing unit mounted on a structure, a plurality of vent holes in said housing unit, a sub-duct having a first and a second opening, a substance to be delivered, and an airflow inside of said structure, said first opening of said sub-duct located inside of said housing unit and said second opening of said sub-duct located in the path of said airflow, said second opening of said sub-duct is oriented with respect to the direction of airflow such that the airflow travels past said second opening and not into said second opening, wherein said method comprises the following steps:

said airflow decreases said pressure in said sub-duct creating a low pressure in said sub-duct, said low pressure causes said air, from an atmosphere outside of the structure, to be drawn through said vent holes into said housing unit and to carry said substance through said sub-duct and into said airflow, and said airflow delivers said substance to said destination.

* * * * *